US012327357B2

(12) United States Patent
Buelow et al.

(10) Patent No.: US 12,327,357 B2
(45) Date of Patent: Jun. 10, 2025

(54) SYSTEMS AND METHODS FOR IMMEDIATE IMAGE QUALITY FEEDBACK

(71) Applicant: KONINKLIJKE PHILIPS N.V., Eindhoven (NL)

(72) Inventors: Thomas Buelow, Grosshansdorf (DE); Tanja Nordhoff, Hamburg (DE); Tim Philipp Harder, Ahrensburg (DE); Hrishikesh Narayanrao Deshpande, Hamburg (DE); Olga Starobinets, Newton, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 387 days.

(21) Appl. No.: 17/782,725

(22) PCT Filed: Dec. 11, 2020

(86) PCT No.: PCT/EP2020/085658
§ 371 (c)(1),
(2) Date: Jun. 6, 2022

(87) PCT Pub. No.: WO2021/122342
PCT Pub. Date: Jun. 24, 2021

(65) Prior Publication Data
US 2023/0029070 A1    Jan. 26, 2023

Related U.S. Application Data

(60) Provisional application No. 62/951,237, filed on Dec. 20, 2019.

(51) Int. Cl.
G06K 9/00 (2022.01)
G06T 7/00 (2017.01)
(Continued)

(52) U.S. Cl.
CPC .............. G06T 7/0014 (2013.01); G06T 7/74 (2017.01); G06V 10/44 (2022.01);
(Continued)

(58) Field of Classification Search
CPC ................ G06T 7/0014; G06T 7/74; G06T 2207/30052; G06T 2207/30068;
(Continued)

(56) References Cited

U.S. PATENT DOCUMENTS 8,737,702 B2   5/2014  Amir
10,064,591 B2  9/2018  Wang
(Continued)

FOREIGN PATENT DOCUMENTS

JP   2003248723 A   9/2003
JP   2013102851 A   5/2013

OTHER PUBLICATIONS

International Search Report and Written Opinion Dated Mar. 25, 2021 for International Application No. PCT/EP2020/085658 Filed Dec. 11, 2020.

*Primary Examiner* — Dhaval V Patel
(74) *Attorney, Agent, or Firm* — Larry Liberchuk

(57) ABSTRACT

An apparatus (1) for providing image quality feedback during a medical imaging examination includes at least one electronic processor (20) programmed to: receive a live video feed (17) of a display (6) of an imaging device controller (4) of an imaging device (2) performing the medical imaging examination; extract a preview image (12) from the live video feed; perform an image analysis (38) on the extracted preview image to determine whether the extracted preview image satisfies an alert criterion; and output an alert (30) when the extracted preview image satisfies the alert criterion as determined by the image analysis.

15 Claims, 3 Drawing Sheets

(51) Int. Cl.
　　　*G06T 7/73*　　　　(2017.01)
　　　*G06V 10/44*　　　(2022.01)
　　　*G06V 30/19*　　　(2022.01)
　　　*G16H 30/20*　　　(2018.01)
　　　*G16H 30/40*　　　(2018.01)

(52) U.S. Cl.
　　　CPC ....... *G06V 30/19007* (2022.01); *G16H 30/20* (2018.01); *G16H 30/40* (2018.01); *G06T 2207/30052* (2013.01); *G06T 2207/30068* (2013.01)

(58) Field of Classification Search
　　　CPC .. G06V 10/44; G06V 30/19007; G16H 30/20; G16H 30/40; G16H 50/20; A61B 8/5215; A61B 8/54; A61B 6/461; A61B 8/461; A61B 6/03; A61B 6/037; A61B 6/5211; A61B 6/54; G06N 3/045
　　　See application file for complete search history.

(56) References Cited

U.S. PATENT DOCUMENTS

| | | | |
|---|---|---|---|
| 2010/0063842 A1 | 3/2010 | Carroll | |
| 2013/0121556 A1* | 5/2013 | Matsumoto | G06T 7/0012 |
| | | | 382/132 |
| 2016/0062956 A1 | 3/2016 | Gotman | |
| 2016/0171682 A1* | 6/2016 | Abedini | G16H 30/20 |
| | | | 382/132 |
| 2017/0265836 A1* | 9/2017 | Laor | A61B 6/582 |
| 2019/0139271 A1 | 5/2019 | Tung | |
| 2019/0261938 A1 | 8/2019 | Sevenster | |
| 2019/0313992 A1 | 10/2019 | Buelow | |

* cited by examiner

SYSTEMS AND METHODS FOR IMMEDIATE IMAGE QUALITY FEEDBACK

CROSS REFERENCE TO RELATED APPLICATIONS

This application is the U.S. National Phase application under 35 U.S.C. § 371 of International Application No. PCT/EP2020/085658 filed Dec. 11, 2020, which claims the benefit of U.S. Provisional Patent Application No. 62/951,237 filed Dec. 20, 2019. These applications are hereby incorporated by reference herein.

FIELD

The following relates generally to the imaging arts, image assessment arts, image quality determination arts, real-time feedback arts, and related arts.

BACKGROUND

Quality management in medical imaging has an increasingly important role. A common approach is to perform periodic quality reviews, in which a small sub-set of imaging examinations performed by an imaging technician are reviewed to assess quality and provide feedback to the imaging technician.

While retrospective quality assessment provides insights into recurring quality issues, immediate alerts regarding quality concerns could enable the technologist to repeat an imaging procedure when necessary while the patient is still present. Close to real-time image quality assessment could be performed using clinical images that are uploaded to the Picturing Archiving and Communication System (PACS) database. However, by the time the clinical images are uploaded, the patient is usually entering the post-examination period and is being unloaded from the imaging device, at which time it is inconvenient or impossible to acquire better quality images.

In another possible approach to provide immediate image quality feedback, the imaging device controller could be modified to perform clinical image quality assessment on the clinical images prior to upload to the PACS. However, such an extensive modification of the imaging device controller might require recertification of the controller, which is a costly process. Moreover, this approach cannot be applied in a modality- and vendor-agnostic manner.

The following discloses certain improvements to overcome these problems and others.

SUMMARY

In one aspect, an apparatus for providing image quality feedback during a medical imaging examination includes at least one electronic processor programmed to: receive a live video feed of a display of an imaging device controller of an imaging device performing the medical imaging examination; extract a preview image from the live video feed; perform an image analysis on the extracted preview image to determine whether the extracted preview image satisfies an alert criterion; and output an alert when the extracted preview image satisfies the alert criterion as determined by the image analysis.

In another aspect, an apparatus for providing image quality feedback on a set of images includes at least one electronic processor; at least one display device; and a video cable splitter via which a live video feed of an imaging device controller is received at the at least one electronic processor. The at least one electronic processor is programmed to: extract a preview image from the live video feed received via the video cable splitter; perform an image quality analysis to on the extracted preview image; and output an alert when the image quality analysis indicates at least one image quality issue.

In another aspect, a method for providing image quality feedback on a set of images includes: tapping a live video feed of an imaging device controller of an imaging device acquiring the images; applying a first trained ML component to detect a preview image from a video frame of the tapped live video feed; applying a second trained ML component to extract the preview image; performing an image analysis on the extracted preview image to determine whether the preview image satisfies an alert criterion; and outputting an alert when the extracted preview image satisfies the alert criterion as determined by the image analysis.

One advantage resides in providing image quality feedback in real time.

Another advantage resides in providing a system to provide image quality feedback in real time without configuring the system for different imaging modalities and models.

Another advantage resides in providing image quality feedback on acquired images of a patient before the patient moves to a post-imaging procedure in a workflow.

Another advantage resides in providing image quality feedback on acquired images of a patient without modifying the imaging device controller to do so.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
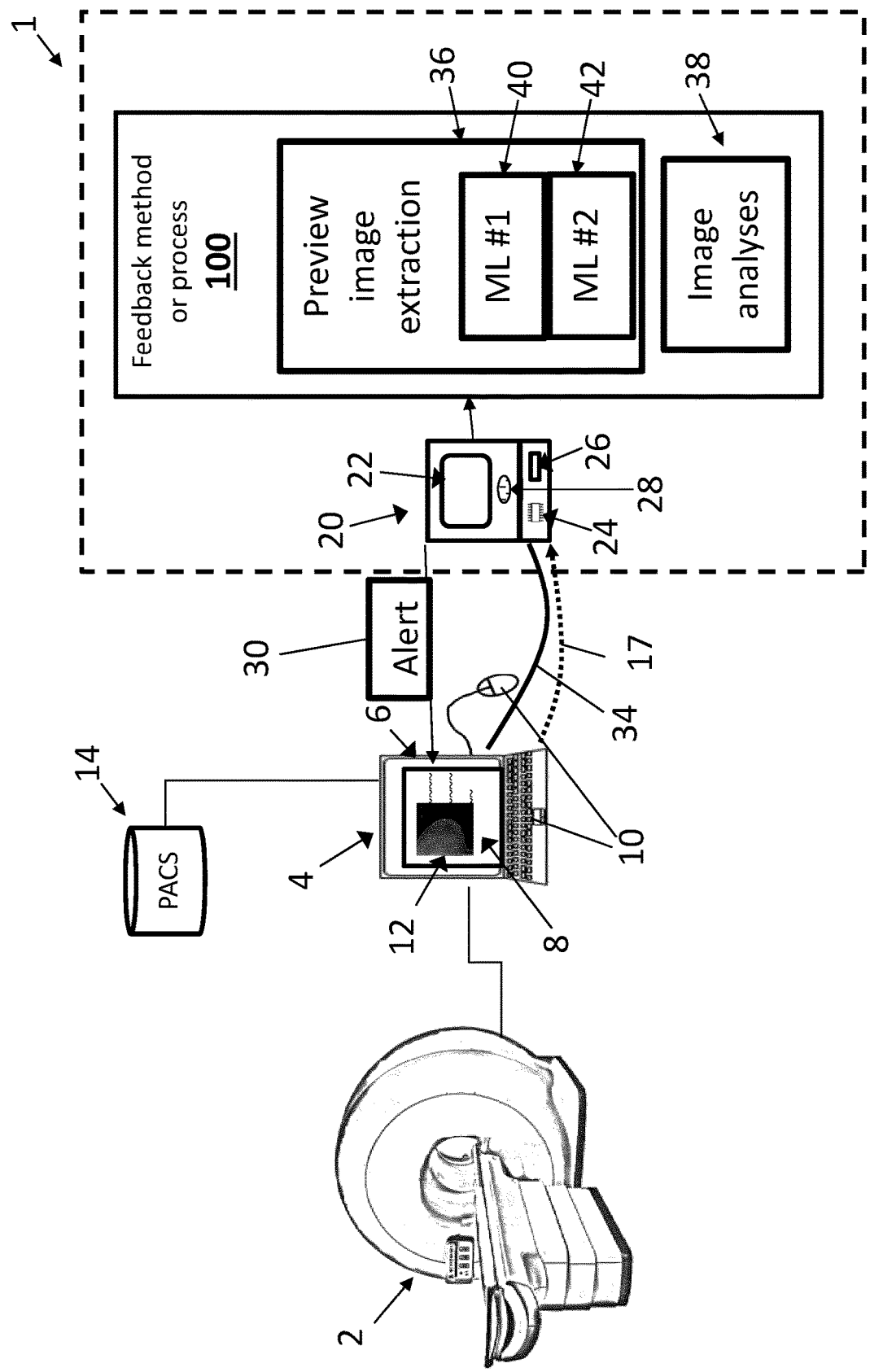
FIG. 1 diagrammatically illustrates an illustrative apparatus for generating benchmarking metrics of current operational workflow performance of a hospital department in accordance with the present disclosure.

The following discloses a system for providing immediate image quality feedback to an imaging technician during an imaging examination. As recognized herein, for many types of image quality assessment, the clinical images are not actually necessary. Rather, low-resolution preview images, which in a typical workflow are acquired prior to acquiring the high resolution clinical images, are actually sufficient to perform the assessment. For example, a low resolution preview image is sufficient to detect image quality issues such as improper patient positioning, improper head angulation in a brain scan, certain motion artifacts, imaging settings that make the anatomical feature of interest too small, detection of occluding medical implants, and so forth.

The disclosed system is configured to tap off the imaging device controller video feed, detect and extract a preview image from the video feed, and perform image quality analyses on the extracted preview image. The video feed can be tapped using a video cable splitter (e.g., a DVI splitter or HDMI splitter depending upon the type of video feed) or by plugging into an "external video out" port if one is available. This approach may be suitable in the case of a compact ultrasound unit with an integrated display, where using a video splitter may not be feasible. Video frames are extracted from the tapped video feed, which provide the basis for the subsequent analysis. As the video feed is typically at 30 frames per second (fps), the analyzed frames are likely to be a fraction of this, e.g. analysis may be at 5 fps for example.

Successive video frames are analyzed to detect and extract the preview image. This entails two parts: (i) determining the modality/anatomy being imaged (unless this information is known a priori, or the system is designed only for use in conjunction with a particular imaging modality and/or imaged anatomy); and (ii) analyzing successive video frames until a preview image is detected and extracted.

The first step (i) can be done in various ways. In one approach, the video frame is processed by optical character recognition (OCR) to detect relevant text identifying the modality and anatomy. This could also entail detecting graphical elements (e.g. vendor logo displayed on screen, vendor-specific terminology, a graphical representation of the imaged anatomy presented by the imaging device controller display, et cetera) by image matching.

Step (ii) then applies a convolutional neural network (CNN) or other machine learning (ML) component trained to detect a preview image in the video frames. It will be noted that the CNN may process many (e.g. hundreds) of video frames until a video frame containing a preview image is detected in the live video feed. (The preceding video frames will typically depict GUI dialogs used in entering patient information and setting up for the imaging examination). Once, a video frame containing a preview image is detected, the preview image is extracted. The detection of a video frame containing a preview image and the extraction of that preview image may be done by the same CNN, or by different CNNs (e.g., a fast first CNN that processes video frames to detect a video frame containing a preview image, and a slower second CNN applied only to that detected video frame to extract the preview image).

The training of the CNN for step (ii) is an empirical process, but the trained CNN is likely to utilize image characteristics for detecting and extracting the preview image such as the preview image being a rectangular gray scale region of the video frame with a dark boundary, along with size characteristics and possibly location characteristics (e.g., a particular vendor may always show preview images on the left side of the screen). In a variant approach, step (i) may use a CNN trained to detect the modality/anatomy. In this variant, the CNNs of steps (i) and (ii) might be combined, so that a single CNN can be applied. Moreover, use of other approaches besides ML is contemplated for performing step (i) and/or step (ii), e.g. a viewport containing the preview image may be detected using pattern recognition or the like.

The extracted preview image is then processed by at least one, and more typically various, modality/anatomy specific machine-learning (ML) components (typically though not necessarily CNNs) that are trained to detect various types of image quality issues (improper patient positioning, improper head angulation, motion blurring, too-small object size, occluding medical implants, et cetera). While ML components are the illustrative embodiment, more generally any type of image processing designed to detect an image quality issue can be applied. For example, motion blurring might be detected by applying an edge detection filter and analyzing edge strength statistics in the edge-filtered image (under the assumption that motion blurring will weaken the edge strength on average). Similarly, image segmentation could be applied to identify the boundary of the anatomy in the image, and this boundary can then be compared against the boundary of the image as a whole to detect image quality issues such as improper patient positioning or image settings that make the image of the anatomy too small. These are merely examples.

When a ML component detects an image quality issue, an alert is issued. In various approaches, this could be a simple textual alert stating the image quality concern accompanied by an audible alarm; up to a complex graphical alert in which the captured preview image is displayed with superimposed graphical annotations highlighting the image quality concern (e.g., if an occluding implant is detected then a superimposed red arrow could point to the implant). In some cases, the alert may provide advice determined from the ML component analysis, e.g. "The patient should be positioned more to the right so as to be centered in the FOV", and/or the guideline position may be indicated by a superimposed box.

The disclosed system can be a computing device (e.g., a notebook computer, Raspberry Pi or other single-board computer, or so forth) and a (possibly integral) display. These components are separate from the imaging device controller, and the system is connected with the video feed of the imaging controller by a DVI splitter or DVI cable. The choice of display depends on the chosen alert presentation, and may range from a compact text-only LCD display for simple textual alerts to a larger color monitor for presenting graphical alerts. Even in the latter case, since the preview images are low resolution (compared with clinical images), the color monitor need not be a large high-resolution monitor; rather, a small 5" or 7" monitor might be sufficient). Optionally, if there is any other type of ancillary computer in the control room that is separate from but located near the imaging device controller, then this computer could be fed the controller video feed and programmed to provide immediate image quality feedback as disclosed.

In some embodiments disclosed herein, the ML components that detect image quality issues could be augmented by additional ML components providing (limited) Computer Aided Diagnosis (CAD) functionality. Because the preview image is of low resolution, these CAD ML components are not envisioned to be used to provide a clinical diagnosis (e.g., for developing a patient therapy), or even a diagnostic recommendation for physician approval. However, the CAD ML components applied to the low resolution preview image are expected to be sufficient to detect certain clinical issues, such as a possible tumor or lesion, an enlarged heart, or so forth, and the corresponding alert might then recommend obtaining immediate radiologist review of the clinical image to assess the detected possible clinical issue before completing the imaging examination. (Alternatively, the alert could recommend acquiring additional clinical images, for example higher resolution images of a detected possible tumor; however, in many imaging laboratories the imaging technician is not permitted to acquire images beyond those specified in the examination order without authorization from a radiologist or the like. Hence, a recommendation to obtain immediate radiologist review may be more appropriate, if the radiologist would have the authority to order the additional imaging).

In other embodiments disclosed herein, if the imaging examination acquires a cinematic (CINE) clinical image sequence and the preview shows a CINE preview image sequence, then the CINE preview image sequence can be extracted from the live video feed. In this case, the extracted CINE preview image sequence can itself be treated as a video segment (i.e. a video segment that is cropped to the preview image viewport, and possibly at a frame rate other than 30 fps or other live video feed frame rate) and fed as input into a suitably trained image quality ML component to detect CINE image quality issues such as using an insufficient CINE frame rate, inadequate detected motion (e.g., in the case of a cardiac CINE image sequence that is expected to capture the beating heart, if insufficient motion is detected this may indicate a problem), or so forth.

With reference to FIG. 1, an illustrative apparatus 1 providing immediate image quality feedback to an imaging technician during an imaging examination is shown. The apparatus 1 is used in conjunction with an image acquisition device 2, which can be (by way of nonlimiting illustrative examples) a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 2 may also be a hybrid imaging device such as a PET/CT or SPECT/CT imaging system. The medical imaging device 2 is controlled via an imaging device controller 4, which includes a display 6 on which a graphical user interface (GUI) 8 is presented to a user (e.g., an imaging technician), and one or more user input devices 10 (e.g. keyboard, trackpad, mouse, et cetera) via which the user interacts sets up and controls the medical imaging device 2 to acquire clinical images.

In the process of setting up to acquire the clinical images, the GUI 8 is operated to cause the medical imaging device 2 to acquire and display a preview image 12. The preview image 12 is usually acquired and displayed at a lower resolution than the clinical image(s) that are subsequently acquired, but is sufficient for the user to verify that the correct anatomy is being imaged, that the anatomy is correctly positioned, is of a usefully large size (but not too large) in the image, and so forth. When the user is satisfied, based on the preview image 12 and other information, that the imaging device 2 is correctly set up to acquire the desired clinical image(s), the user operates the GUI 8 to initiate the clinical imaging, reviews the acquired clinical images on the display 6, and ultimately stores the final clinical images to a Picturing Archiving and Communication System (PACS) 14 or other clinical images repository.

FIG. 1 also shows the apparatus 1 for providing immediate image quality feedback to the user (e.g. imaging technician) during the imaging examination. The apparatus 1 is preferably, although not necessarily, a separate device from the imaging device controller 4. For example, the apparatus 1 may comprise a computer 20 embodied as a notebook computer, tablet computer, a Raspberry Pi or other single-board computer, or so forth) and includes a display 22, an electronic processor (e.g. one or more microprocessors) 24 and a non-transitory storage medium 26. (Note, the electronic processor 24 and a non-transitory storage medium 26 are diagrammatically shown in FIG. 1, but are typically internal components, e.g. housed inside the housing of the computer 20). The display 22 presents one or more alerts 30 when a possible image quality issue is detected. Optionally, the apparatus 1 further includes a loudspeaker 28, e.g. mounted in or on the computer 20, for providing an audible indication when an alert 30 is presented.

While the apparatus 1 typically employs a standalone computer 20 or the like as the data processing device, it is contemplated for some data processing involved in providing the immediate image quality feedback (for example, computationally complex image analyses) to be implemented on a remote server (not shown) that is connected with the local electronic processing device 20 via a wired or wireless data communication connection. the remote server may be a hospital server, cloud computing resource, or so forth connected with the local computer 20 via a hospital electronic network and/or the Internet. For example, the standalone computer 20 is in communication with one or more imaging device controllers 4 (operated by a corresponding number of local operators or technicians). The standalone computer 20 monitors images acquired at each location of the one or more imaging device controllers 4, and can issue respective alerts 30 for each corresponding local operator when an image quality issue is detected at that local operator(s)' site.

The display device 22 can be of any size, but to provide the apparatus 1 as a compact unit that can be conveniently positioned next to (or otherwise near to) the imaging device controller 4, the display 22 is typically relatively small, e.g. a 5-inch display, 10-inch display, 12-inch display, or so forth. In some embodiments, the standalone computer 20 does not have any user input devices (i.e., nothing analogous to the keyboard, mouse, or other user input device 10 of the imaging device controller 4), although it is alternatively contemplated for the computer or other electronic processing device 20 to include a keyboard or the like for setting up the image quality feedback software or for other purposes. The non-transitory storage medium 26 may, by way of non-limiting illustrative example, comprise one or more of a hard disk or other magnetic storage medium, a solid state drive (SSD), flash memory, or other electronic storage medium, an optical disk or other optical storage medium, various combinations thereof, and/or so forth.

The electronic processing device 20 of the immediate image quality feedback apparatus 1 is operatively connected to receive a live video feed 17 of the display 6 of the imaging device controller 4. The live video feed 17 is, in the illustrative embodiment, provided by a video cable splitter 34 (e.g., a DVI splitter, a HDMI splitter, and so forth). In other embodiments, the live video feed 17 may be provided by a video cable connecting an auxiliary video output (e.g. aux vid out) port of the imaging device controller 4 to the electronic processing device 20 of the immediate image quality feedback apparatus 1. This latter approach may be useful, for example, if the imaging device 2 is a compact ultrasound imaging device with an integral display, in which case it may not be convenient to connect a video cable splitter since the wiring of the display is in this case the wiring to the ultrasound display is entirely internal to the ultrasound imaging device cabinet—but, an "aux vid out" port may be provided in such a portable ultrasound imaging device. In another contemplated embodiment, screen-sharing software running on the imaging device controller 4 and the electronic processing device 20 provides the live video feed 17 to the electronic processing device 20. These are merely illustrative examples.

The non-transitory storage medium 26 of the immediate image quality feedback apparatus 1 stores instructions which are readable and executable by the at least one electronic processor 24 of the apparatus 1 (which as previously noted, is contemplated to include a remote server or servers on a local area network or the Internet) to perform disclosed operations including performing a method or process 100 for providing immediate image quality feedback to an imaging technician during an imaging examination. The feedback method or process 100 includes a preview image extractor method or (sub-)process 36, and one or more image analyses 38, In some embodiments, the at least one electronic processor 20 of the workstation 12 is programmed to implement at least one machine-learning ML component 40, 42 (e.g., one or more convolutional neural networks (CNNs) to extract the preview image 12 from the tapped live video feed 17. In some examples, a first trained ML component 40 is programmed to detect the preview image 12 in a frame of the live video feed 17, while a second ML component 42 is programmed to extract the preview image 12 from that frame of the live video feed. In some examples, the method 100 may be performed at least in part by cloud processing. In some examples, the method 100 may be performed at least in part by cloud processing.

Figure 2:
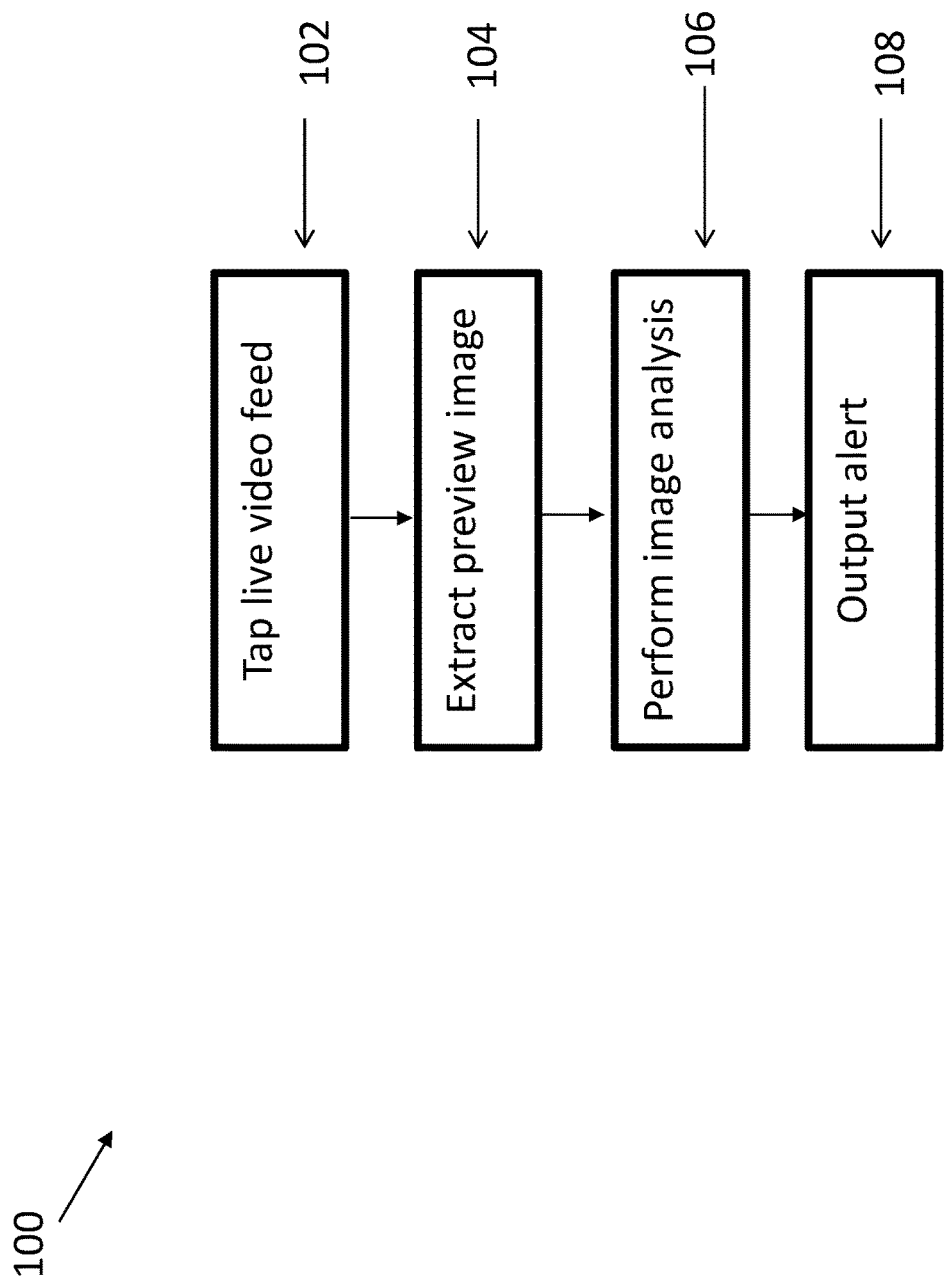
FIG. 2 shows example flowchart operations performed by the apparatus of FIG. 1.

With reference to FIG. 2, and with continuing reference to FIG. 1, an illustrative embodiment of the method 100 is diagrammatically shown as a flowchart. The method 100 is performed over the course of a medical imaging examination performed using the medical imaging device 2. At an operation 102, the electronic processing device 20 is programmed to receive the live video feed 17 of the imaging device controller 10 of the medical imaging device 2, e.g. via the video cable splitter 34.

At an operation 104, the electronic processing device 20 is programmed to extract the preview image 12 from a video frame of the tapped live video feed 17 that contains the preview image. To do so, the at least one electronic processor 20 is programmed to determine at least one of a modality of the imaging device 2 and/or an anatomy of a patient being imaged by the imaging device. For example, an OCR process can be performed on the live video feed 17 to relevant text identifying the modality and/or the anatomy. In another example, an image matching process can be performed on the live video feed 17 to graphical elements identifying the modality and/or the anatomy.

The operation 104 advantageously enables the apparatus 1 to be used in conjunction with numerous different modalities/imaged anatomies. In one example, the detected modality can be mammography, in which positioning quality is assessed by known methods involving the detection and evaluation of anatomic landmarks (e.g., pectoral muscle, skin-line, nipple, infra-mammary angle, and so forth). In another example the detected modality can be radiography, and the detected anatomy is a chest, in which, after automatic identification of the lung area, the clavicles and the ribs, the field of view, the angulation of the patient and the inhalation state are evaluated. In a further example, the detected modality can be CT, and the detected modality can be a head, in which a correctness of patient positioning can be assessed given a sagittal slice. These are merely non-limiting examples. In an alternative approach, if the apparatus 1 is designed to work with only a specific imaging modality then there is no need to determine the modality, and this aspect of operation 104 can be omitted. Likewise, if the apparatus 1 is designed to work with only a specific imaged anatomy (e.g., in the case of a dedicated mammography imaging system, the anatomy is a breast) then there is no need to determine the imaged anatomy, and this aspect of operation 104 can be omitted.

Based on the determined modality or imaged anatomy part, video frames from the tapped live video feed 17 are analyzed to detect the video frame containing the preview image 12. To do so, the at least one trained ML component (e.g., CNN) 40, 42 is applied to the tapped live video feed 17 to detect and extract the preview image 12. In one example, the CNN 40, 42 is configured to detect the preview image 12 by identifying, in the tapped live video feed 17, at least one of: a rectangular gray scale region with a dark boundary, size characteristics of a preview image, and location characteristics of a preview image. In another example, the first CNN 40 is applied to detect the preview image 12 in a video frame of the tapped live video feed 17, and the second CNN 42 is applied to extract the preview image.

At an operation 106, the workstation 12 is programmed to perform an image analysis 38 to on the extracted preview image 12 to determine whether the preview image satisfies an alert criterion. Typically, the image analysis 38 is an image quality analysis performed on the extracted preview image 12 to determine whether the extracted preview image has an image quality issue. For example, the image quality analysis may comprise applying the at least one trained ML component 40, 42 to the extracted preview image to determine whether the extracted preview image 12 has the image quality issue. In another example, the image quality issue comprises image blurring and the image quality analysis comprises analyzing edge strength statistics in the preview image 12 filtered by an edge to detection filter to detect motion blurring in the preview image. In another example, the image quality issue comprises improper patient positioning and the image quality analysis comprises identifying an anatomy boundary in the preview image and comparing the anatomy boundary to a remainder of the image to detect improper patient positioning in the imaging device 2. In another example, the image quality issue comprises a sizing issue and the image quality analysis comprises identifying an anatomy boundary in the preview image 12 and comparing the anatomy boundary to a remainder of the image to detect an anatomy image size below a size threshold. In another example, the image quality issue comprises an occluding implant and the image quality analysis comprises identifying an implant in the preview image 12, identifying anatomy of interest in the preview image, and detecting the identified implant occluding the identified anatomy of interest in the preview image. These are merely illustrative examples of image quality analyses for detecting various image quality issues. It will be appreciated that the operation 106 may perform various image quality analyses to detect various types of image quality issues, so as to provide comprehensive immediate image quality feedback. In some embodiments, the image analysis is selected based on the determined modality and/or imaged anatomy (at the operation 104).

To provide additional and/or alternative functionality, the image analysis 106 may optionally comprises a Computer Aided Diagnosis (CAD) image analysis to detect the alert criterion comprising a proposed clinical diagnosis output by the CAD image analysis. Examples of a clinical diagnosis can include one or more messages, such as, for example, indicating "Possible lesion detected in lung. Recommend having radiologist review before completing the imaging examination." or "Possible aortic stenosis detected. Recommend having radiologist review before completing the imaging examination."

In some embodiments, the extracting operation 104 includes extracting the preview image 38 comprising a cinematic (CINE) preview image sequence comprising a plurality of successive video frames from the tapped live video feed 17. In such cases, the image analysis operation 106 may include performing the image analysis on the extracted CINE preview image 38 to determine whether the preview image satisfies an alert criterion. For example, the image analysis may be performed on the extracted cinematic preview image to determine whether an anatomical movement captured by the extracted cinematic preview image satisfies the alert criterion (e.g., too much movement, or too little movement, depending upon the clinical application to which the imaging is directed). Some non-limiting examples of anatomical movement can be cardiac cycling movement, and the alert criterion might be if the strength the cardiac cycling movement captured by the cinematic preview is too weak (or too strong, if the goal is to image a region that is not affected by the cardiac cycling movement).

At an operation 108, the workstation 12 is programmed to output the alert 30 when the extracted preview image satisfies the alert criterion as determined by the image analysis. To do so, the image analysis is performed to detect at least one image quality issue in the extracted preview image 38. The CNN 36 can be applied to detect the at least one image quality issue. For example, the CNN 36 is programmed to perform operations including: (i) analyzing edge strength statistics in the preview image filtered by an edge to detection filter to detect motion blurring in the preview image 38; (ii) identifying an anatomy boundary in the preview image and compare the anatomy boundary to a remainder of the image to detect improper patient positioning in the imaging device 2; (ii) identifying an anatomy boundary in the preview image and compare the anatomy boundary to a remainder of the image to detect image settings below a size threshold; and so forth.

The alert 30 is output to indicate that the at least one image quality issue satisfies the alert criterion. The alert 30 can be any suitable alert, including, for example, a textual alert on the display device 24 of the workstation 12 or the screen 32, an audible alarm via the loudspeaker 28, graphical annotations on the extracted preview image displayed on the display 22 of the apparatus 1, and so forth.

Figure 3:
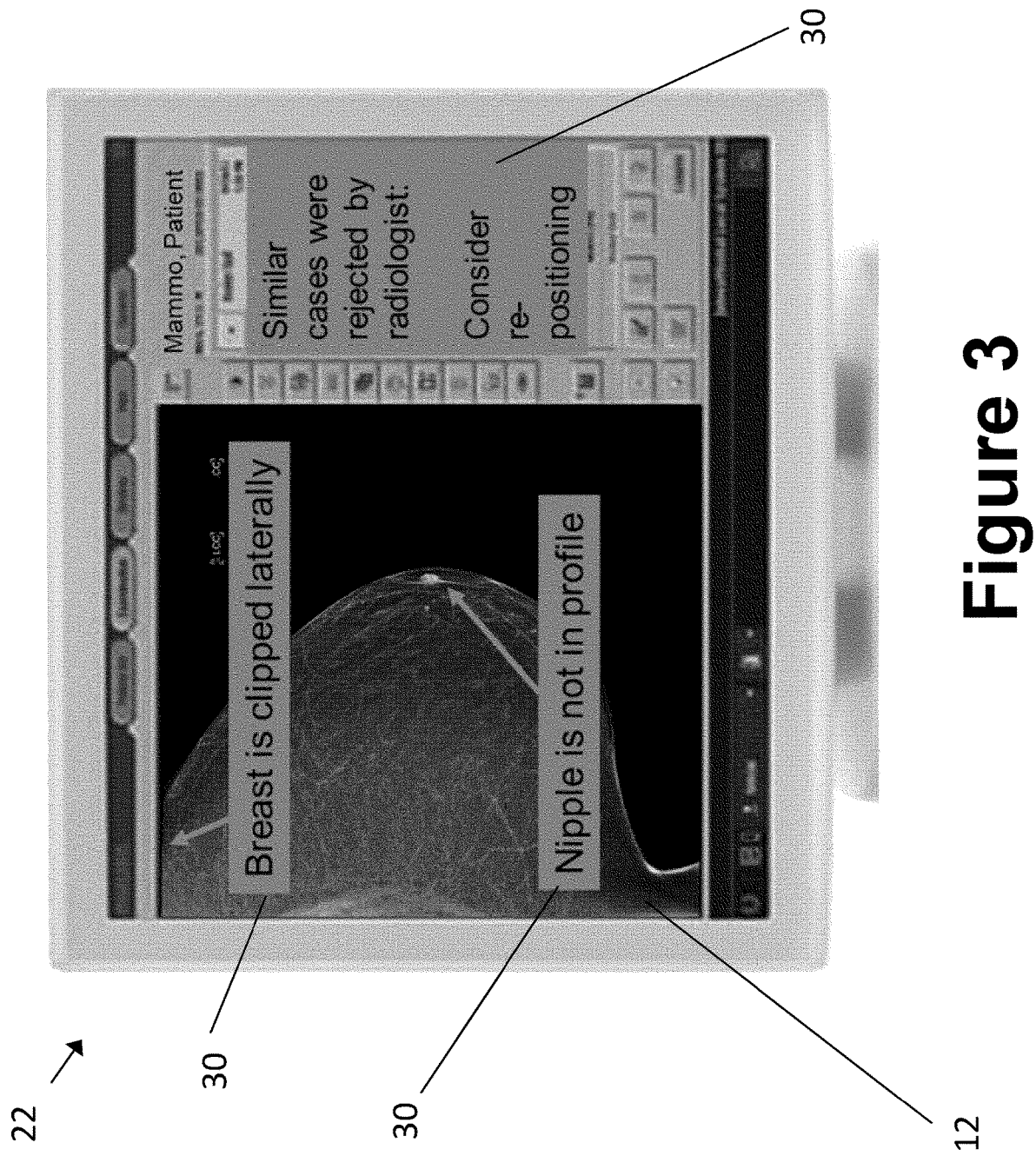
FIG. 3 shows an example of alerts displayed on the apparatus of FIG. 1.

FIG. 3 shows an example of the alert 30 as shown on the display device 22. As shown in FIG. 3, the alert 30 can be textual messages (e.g., "breast is clipped laterally", "nipple is not in profile", and so forth). In addition, the alert 30 can include advice for the local operator of the imaging device 2 to resolve the issues (e.g., "consider re-positioning).

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus for providing image quality feedback during a medical imaging examination, the apparatus comprising at least one electronic processor programmed to:
   receive a live video feed of a display of an imaging device controller of an imaging device performing the medical imaging examination;
   extract a preview image from the live video feed by determining an anatomy of a patient being imaged by the imaging device, analyzing video frames of the live video feed to detect a video frame containing the preview image, and extracting the preview image from the detected video frame;
   perform an image analysis on the extracted preview image to determine whether the extracted preview image satisfies an alert criterion, comprising performing an image quality analysis on the extracted preview image to determine whether the extracted preview image has an image quality issue; and
   output an alert when the extracted preview image satisfies the alert criterion as determined by the image analysis, comprising outputting the alert indicating the image quality issue when the extracted preview image has the image quality issue as determined by the image quality analysis.

2. The apparatus of claim 1, wherein extraction of the preview image comprises:
   determining a modality of the imaging device.

3. The apparatus of claim 2, wherein determining at least one of a modality of the imaging device and an anatomy of a patient being imaged by the imaging device includes at least one of:
   performing an optical character recognition (OCR) process on the live video feed to detect relevant text identifying the modality and/or the anatomy; and
   performing an image matching process on the live video feed to detect graphical elements identifying the modality and/or the anatomy.

4. The apparatus of claim 2, wherein the analyzing of the live video feed and the extracting of the preview image includes:
   applying at least one trained machine-learning (ML) component to video frames of the live video feed to at least one of detect the video frame containing the preview image and extract the preview image.

5. The apparatus of claim 4, wherein applying at least one trained ML component includes:
   applying a first trained ML component to detect the video frame containing the preview image; and
   applying a second trained ML component to extract the preview image from the detected video frame.

6. The apparatus of claim 1, wherein the at least one electronic processor is further programmed to:
   select the image analysis based on the determined modality and/or anatomy.

7. The apparatus of claim 1, wherein the image quality analysis comprises applying at least one trained ML component to the extracted preview image to determine whether the extracted preview image has the image quality issue.

8. The apparatus of claim 7, wherein the image quality issue comprises image blurring and the image quality analysis comprises:
   analyzing edge strength statistics in the preview image filtered by an edge to detection filter to detect motion blurring in the preview image.

9. The apparatus of claim 1, wherein the image quality issue comprises improper patient positioning and the image quality analysis comprises:
   identifying an anatomy boundary in the preview image and comparing the anatomy boundary to a remainder of the image to detect improper patient positioning in the imaging device.

10. The apparatus of claim 1, wherein the image quality issue comprises a sizing issue and the image quality analysis comprises:

identifying an anatomy boundary in the preview image and comparing the anatomy boundary to a remainder of the image to detect an anatomy image size below a size threshold.

11. The apparatus of claim 1, wherein the image quality issue comprises an occluding implant and the image quality analysis comprises:

identifying an implant in the preview image, identifying anatomy of interest in the preview image, and detecting the identified implant occluding the identified anatomy of interest in the preview image.

12. The apparatus of claim 1, wherein the image analysis comprises a Computer Aided Diagnosis (CAD) image analysis to detect the alert criterion comprising a proposed clinical diagnosis output by the CAD image analysis.

13. The apparatus of claim 1, wherein:

the extracting includes extracting the preview image comprising a cinematic preview image sequence from the live video feed; and the performing of the image analysis comprises performing the image analysis on the extracted cinematic preview image to determine whether an anatomical movement captured by the extracted cinematic preview image satisfies the alert criterion.

14. The apparatus of claim 1, further including:

at least one display device that is not a display of the imaging device controller; and a video cable splitter via which the at least one electronic processor receives the live video feed of the imaging device controller.

15. A computer implemented method for providing image quality feedback on a set of images, the method comprising:

tapping a live video feed of an imaging device controller of an imaging device acquiring the images;

applying a first trained machine learning (ML) component to detect a preview image from a video frame of the tapped live video feed;

applying a second trained ML component to extract the preview image by determining an anatomy of a patient being imaged by the imaging device, analyzing video frames of the live video feed (17) to detect a video frame containing the preview image, and extracting the preview image from the detected video frame;

performing an image analysis on the extracted preview image to determine whether the preview image satisfies an alert criterion, comprising performing an image quality analysis on the extracted preview image to determine whether the extracted preview image has an image quality issue; and outputting an alert when the extracted preview image satisfies the alert criterion as determined by the image analysis, comprising outputting the alert indicating the image quality issue when the extracted preview image has the image quality issue as determined by the image quality analysis.

* * * * *